United States Patent [19]

Douglas et al.

[11] Patent Number: 5,006,109
[45] Date of Patent: Apr. 9, 1991

[54] METHOD AND DEVICE FOR CONTROLLING PRESSURE, VOLUMETRIC FLOW RATE AND TEMPERATURE DURING GAS INSUFFICATION PROCEDURES

[75] Inventors: Donald D. Douglas, 703 White Swan Dr., Arnold, Md. 21012; James A. Hamel, Virginia Beach, Va.

[73] Assignee: Donald D. Douglas

[21] Appl. No.: 406,351

[22] Filed: Sep. 12, 1989

[51] Int. Cl.$^5$ ............................................. A61M 13/00
[52] U.S. Cl. ........................................ 604/26; 128/747
[58] Field of Search .............. 128/3, 4, 8, 747, 202.24, 128/203.12, 203.17, 203.18, 203.26, 204.17, 204.18, 204.22, 205.23, 203.14; 604/23-26

[56] References Cited

U.S. PATENT DOCUMENTS

| | | | |
|---|---|---|---|
| 1,682,344 | 8/1928 | Lesieur | 604/26 |
| 2,579,113 | 12/1951 | Gardner | 128/747 |
| 3,481,323 | 12/1969 | Cook et al. | |
| 3,674,010 | 7/1972 | Falenks | 128/747 |
| 3,782,363 | 1/1974 | Davis | 128/747 |
| 3,870,072 | 3/1975 | Lindemann | |
| 3,871,371 | 3/1975 | Weigl | 128/205.23 X |
| 3,885,590 | 5/1975 | Ford et al. | 137/613 |
| 3,982,533 | 9/1976 | Weist | |
| 4,048,992 | 9/1977 | Lindemann et al. | |
| 4,063,548 | 12/1977 | Klatt et al. | |
| 4,207,887 | 6/1980 | Hiltebrandt et al. | 604/26 |
| 4,621,633 | 11/1986 | Bowles et al. | 128/203.17 |
| 4,676,774 | 6/1987 | Semm et al. | |
| 4,735,603 | 4/1988 | Goodson et al. | |
| 4,874,362 | 10/1989 | Wiest et al. | 604/26 |

FOREIGN PATENT DOCUMENTS

729352 5/1955 United Kingdom .................. 604/23

Primary Examiner—C. Fred Rosenbaum
Assistant Examiner—Corrine Maglione
Attorney, Agent, or Firm—Mason, Fenwick & Lawrence

[57] ABSTRACT

A system for administering gas to a patient during an endoscopic or medical procedure includes elements for regulating the temperature, pressure, and volumetric flow rate of the gas. A gas source operating with a heated pressure regulator and filter provide a smoothly regulated flow of any medically necessary gas, such as $CO_2$, to a main body of the gas delivery system. The main body comprises a primary heater for control of the temperature of the gas administered to the patient, a fine pressure regulator for controlling its pressure in a safe manner, and a flow regulator for controlling its volumetric flow rate. Temperature, pressure, and volumetric flow rate indicators allow the physician continuous monitoring of the quantitative status of each of these important physiologic parameters; this data may also be recorded for documentation purposes. The system allows increased safety in endoscopic or medical procedures in which gas is used, greater operational convenience for the physician, enhanced quantitative observation and documentation capability, while retaining flexibility in using conventional alternate gas sources.

41 Claims, 1 Drawing Sheet

METHOD AND DEVICE FOR CONTROLLING PRESSURE, VOLUMETRIC FLOW RATE AND TEMPERATURE DURING GAS INSUFFLATION PROCEDURES

BACKGROUND OF THE INVENTION

1. Field of the Invention

The present invention relates to the field of medical devices, in general, and, in particular, to a gas delivery system for use in medical or veterinary procedures which require the introduction of a gas into a human or animal body, or to create or maintain a controlled gas environment. More specifically, the invention is applicable to devices and methods for safely administering gases to patients for insufflation of organs, such as during endoscopic procedures.

2. Related Art

Endoscopy is an important procedure for the effective diagnosis and treatment of many disorders, and is particularly useful in diagnosing and treating various gastrointestinal disorders. Successful inspection of the gastrointestinal tract is dependent upon both the expertise of the physician and the quality of the endoscopic instruments and accessories used in the procedure. Two particular types of endoscopes used in the field of gastroenterology are the gastroscope for upper intestinal visualization, and the colonoscope for the visualization of the colon.

During an endoscopic procedure, the endoscope is attached to a light source to illuminate the area under examination. The endoscope then transmits an image of the inside of a patient's bowel to the physician via either fiber optic bundles or a microchip-based communication system. The endoscope also provides a conduit for the delivery of a gas to insufflate the bowel to facilitate examination. Both light and gas are thus critical to successful completion of all diagnostic or therapeutic endoscopic procedures.

Known endoscopic devices utilize an air compressor which is housed inside a light source to deliver the gas. Limits for the volume and pressure of the delivered gas are pre-set in the compressor at the time it is manufactured. The temperature of the delivered gas is not controlled in known systems, and varies according to the ambient air temperature and any negligible heat which may be generated during compression of the air by the internal air compressor.

Since known systems do not provide a quantitatively accurate system within the light source for accurately regulating the delivery of the gas, there can be large variations in the pressure, volume and temperature of gas administered during an endoscopic procedure. A physician who uses a standard light source during an endoscopic procedure must rely upon the pre-set adjustments of the internal air compressor which, generally, only allows adjustments to settings of "low," "medium," "high" and "off." The instruments are not provided with means to finely calibrate the pressure and volume of the gas. Furthermore, the air compressors of known systems operate by compressing air in a series of spurts or pulses due to reciprocating action, potentially causing unwanted variation in actual pressure delivered. Thus, a physician cannot determine or accurately control the exact volume or pressure of the gas which is being used to insufflate a patient's bowel during the procedure. No instruments are now available to record these variables for documentation in a patient's chart.

Moreover, known gas delivery systems are not provided with a means to control the temperature of the gas delivered to a patient. Under Boyle's and Charles' Laws, it is known that the variables of pressure of a gas in a constant volume is proportional to the temperature of gas. Thus, known systems which do not regulate the temperature of the gas being administered lose thermodynamic control over the performance of the gas delivery system.

It is therefore desirable to provide a gas delivery system in which the pressure, volume, and temperature are all quantitatively controlled, regulated, and capable of being monitored by the physician for the safety of the patient.

It is known that air pressure is a cause of a potentially fatal perforation of a colon during a colonoscopic examination, or may cause the development of late perforations. Dr. R.A. Kozarek et al, in an article entitled "Air Pressure Induced Colon Injury During Diagnostic Colonscopy," *Gastroenterology* 78:7-14 (1980) cites that, using four different light sources and determining pressure needed to perforate the colons of dogs, pigs, human cadavers and in vivo human investigation, all four of the light source machines used are capable of delivering pressure that exceed the rupture point in all but the dog's colon. (The dog's colon could not be perforated, possibly because is has two layers of smooth muscle, in contrast to human and pig colons only having one layer of smooth muscle, plus taenia coli.) Therefore, rupture of the human colon is a very real possibility using known light source machines, as the pressure, volume, and temperature of the insufflating gas are not accurately controllable.

For these reasons also, it is desirable to provide a gas delivery system to the endoscopic device in which the delivered gas is reliably regulated so as to minimize possible injury caused by gas.

Another safety factor is the lack of a voltage regulator on the known light sources. Electrical power fluctuations during an endoscopic procedure present a danger to the patient. A power surge may cause the air compressor to function abnormally by putting out transient increased volumes or pressures of the delivered ambient air. If a colonoscope were in a particularly delicate orientation (such as in a diverticulum, in a delicate "slide-by" during the procedure, or in a fixed or partially obstructed loop of bowel), this increased pressure could cause a serosal tear, perforation or sub-mucosal infiltration of gas.

Other phenomena contribute to possible danger to patients. A valsalva maneuver, if performed by the patient during an examination, can increase the pressure in a colon by an average of 38 mm Hg. Furthermore, external pressure exerted by the examining physician to expedite movement of the colonoscope through the bowel can exert up to an average of 17 mm Hg. These pressures are additive to the intraluminal pressure already present in the colon during colonoscopy, so that any pressure component added by the gas delivery system risks pushing the total pressure over a threshold where injury will occur.

Therefore, it is desirable, when using a pressurized gas delivery system, to prevent unwanted transient increases in pressure, as this prevention would guard the safety of the patient.

It is known that the endoscopic use of gas such as ambient air interferes with other diagnostic procedures such as barium enemas which might need to be performed the same day on a patient. Furthermore, just performing a colonoscopic procedure can usually stop fairly brisk diverticular bleeding of the colon, but that, unfortunately, the exact site of bleeding cannot therefore usually be found. This stoppage of diverticular bleeding defeats the purpose of the diagnostic procedure. The cause of this defeat of the diagnostic procedure may be that the insufflation and distention of the bowel lumen with ambient air or a barium examination with cold barium may cause the small bleeding vessels to go into spasm and stop bleeding, perhaps for hours after the examination.

In this case, the reduced usefulness of bleeding scans or arteriograms are due to the amount of air or barium which is left in the gastro-intestinal tract after the examination. If surgery is elected as a subsequent step, a surgeon does not know accurately the point in the bowel where the patient is bleeding. Surgical intervention may result in the removal of an unnecessarily large segment of bowel, or a sub-total colectomy, because of an inadequate diagnostic procedure.

Therefore, it is desirable to use a gas at a controlled volume, pressure and temperature which does not interfere with any diagnostic procedures conducted in conjunction with the gas delivery system.

Although ambient air generally is used when delivering a gas to a patient through a gastroscope or a colonoscope, carbon dioxide ($CO_2$) gas is used to great advantage as an alternative gas insufflation source when performing a colonoscopy. The advantages of using $CO_2$ gas for routine colonoscopy are significant. For instance, $CO_2$ gas reduces the likelihood of an explosion of volatile gas which may be present in the colon when electro-coagulating equipment is used during a procedure. Also, since $CO_2$ is rapidly absorbed from the intestines in less than one hour after the procedure is performed, it is possible to schedule additional necessary procedures (such as an X-ray, an ultrasound or a CT scan) the same day after the colonoscopy. Presently, this is not the case in the use of ambient air.

The virtual elimination of a potential explosion of a volatile gas in the colon is an advantage which applies both to patients who have not been adequately prepared for an examination, or to those who have inadvertently consumed a fermentable food substance in the time period preceding the colonoscopy. That $CO_2$ should be used for all colonoscopies is a statement which has been made by some of the leading endoscopists in the world. The logic is not just that the use of $CO_2$ is a "fire extinguisher." The use of $CO_2$, as will be discussed in greater detail below, has advantages over insufflation with ambient air for all patients, even for those in whom combustion is not a danger.

Hussein, A.M.J. et al, in an article entitled "Carbon Dioxide Insufflation For More Comfortable Colonoscopy," *Gastrointestinal Endoscooy* 30:68-70 (1984), documents that patients who receive $CO_2$ as the sole insufflation gas source have less discomfort and less flatus from the examination. Also, patients reabsorb the $CO_2$ gas within approximately one-half hour after the examination, facilitating further endoscopic examination or other tests such as barium enemas, CT scans, ultrasound tests or arteriograms. These tests can be performed the same day as the colonscopy.

The use of $CO_2$ also provides benefits in the field of radiology as well as for colonoscopy. Patient comfort, fast reabsorption and adequacy as a gas source for double-contrast barium enema studies are included. $CO_2$ is inexpensive and is sterile. It causes less discomfort during and after a colonoscopic procedure, as evidenced by a study of over 5000 colonoscopy patients by B. H. Rogers, M.D., reported in *Gastrointestinal Endoscooy* 31:108-9 (1985). Other articles cite no contraindication in the use of $CO_2$ in patients with serious lung disease. Studies monitoring arterial blood gas confirm the safety of this gas for colonoscopic examination in patients even with lung disease.

Significantly, the use of $CO_2$ increases blood flow to the colon, and increases the amount of $pO_2$ in the perivascular areas, apparently due to the dissociation of the oxy-hemoglobin curve in the *colonic mucosa*. Ambient air, on the other hand, which comprises 80% nitrogen, causes both increased and sustained intraluminal pressure and significantly decreases blood flow to the colon. As noted by Christopher B. Williams, increased blood flow to the colon, using $CO_2$, may facilitate determination of the source and potentiate endoscopic treatment of lower gastro-intestinal bleeding in patients with diverticular or arterial-venous malformations.

Therefore, it is desirable to use a gas which has minimal detrimental and undesirable physiologic effects, so that the patient is examined and treated under physiologic, or near-physiologic, conditions.

Even if $CO_2$ is presently used in a procedure using the known delivery system, certain shortcomings exist. These include poorly controlled pressure and volume regulators, clumsy manual irrigation of the distal lens system, awkward placement of the $CO_2$ button on the colonoscope, inadvertent injection of small metal flakes from the $CO_2$ cylinder into the colonoscope's insufflation tubing, potential freeze-up of the $CO_2$ valve nozzle, fluctuation of $CO_2$ gas pressure (sputtering), accidental injection of liquid $CO_2$ into the colonoscope itself, or, potentially, into the patient.

In known $CO_2$ delivery systems, the $CO_2$ is administered by connecting an external $CO_2$ gas cylinder pressure regulator, via plastic tubing, directly to a $CO_2$ insufflation valve device on the colonoscope. However, since the $CO_2$ insufflation valve is not conveniently located on the colonoscope, it is awkward to use by the physician performing the procedure. With the use of the inventive device (described below), the $CO_2$ valve is no longer required. $CO_2$ now passes through the usual air insufflation pathway, thus bypassing the air compressor.

Further, $CO_2$ gas delivered in the known delivery manner during a colonoscopy is not regulated by the internal gas compressor of the light source as it would if ambient air were being employed. The physician must manually adjust the pressure valve settings on the $CO_2$ cylinder itself, leaving many inherent possibilities for error due to imprecise pressure gauges and volume regulators on the $CO_2$ cylinder.

Of particular concern, even when a $CO_2$ gas source is employed, is the lack of any means to control its temperature. Without temperature control, the volume and/or the pressure of the insufflated gas will increase after the gas has entered the lumen of the bowel due to heating of the gas by the body itself. This is non-physiologic and potentially harmful to the patient. As in systems where ambient air is employed, insufficient control over the gas temperature, pressure, and volume can cause over-distension or even perforation of the bowel.

Thus, a need exists for a system and method for administering gas to a human or animal body which provides a means to accurately determine and control the temperature, volume and pressure of the gas being delivered to the patient. It is desirable that the system be both comfortable in its use for the physician, and also use the standard air insufflation pathway without using the light source air compressor. Determination and control of all three of these parameters constitutes determination and control of three independent variables in Boyle's and Charles' Laws.

Currently, upper endoscopy has no means to use $CO_2$ for insufflation. An accurate control system would make it possible to use $CO_2$ gas when performing upper endoscopy, which has many of the same advantages discussed for colonoscopy.

More generally, a need exists for a system which overcomes the above-described limitations, whether $CO_2$ or another gas is used for insufflation.

SUMMARY OF THE INVENTION

It is an object of the present invention to provide a delivery system for safely administering gas to a patient during an endoscopic procedure.

An additional object of the present invention is to provide a gas delivery system which is easily adapted to any device in the medical or veterinary field which utilizes gas.

An additional object of the present invention is to provide a gas delivery system which minimizes the occurrence and magnitude of transient increases/decreases in gas pressure.

An additional object of the present invention is to provide a gas delivery system which minimizes detrimental stresses on the human body during an endoscopic or medical procedure in which the gas delivery system is involved.

An additional object of the present invention is to provide a gas delivery system which minimally interferes with the operation or results of a diagnostic or therapeutic procedure conducted in conjunction with the gas delivery system.

An additional object of the present invention is to provide a gas delivery system which is convenient to operate.

It is another object of the present invention to provide a gas delivery system which permits the use of one or more non-combustible gases or medically required gases during a procedure by using a selection control on the device.

A further object of the present invention is to provide a gas delivery system which can be easily transported from place to place and which attaches to a light source or other medical equipment and is easily connected to the system.

It is yet a further object of the present invention to provide a delivery system for administering gas to a patient which accurately and independently regulates the temperature, pressure and volume of the gas being administered during an endoscopic or medical procedure.

An additional object of the present invention is to provide a gas delivery system which allows the user to finely adjust the temperature, pressure and volume of a gas as the gas is administered to a patient during an endoscopic or medical procedure.

Yet a further object of the present invention is to provide a gas delivery system which includes a heater having an accurate adjustable control for the temperature of the gas, and an accurate adjustable fine pressure regulator and flow regulator, for controlling pressure, volumetric flow rate, and temperature when delivering gas to a patient during an endoscopic or medical procedure.

Another object of the present invention is to provide a method of gas delivery, in the medical field, having at least the same objects and advantages provided by the inventive gas delivery system described herein for the control of pressure, volume and temperature of a delivered gas.

The present invention provides a novel system for administering gas to a patient during, for example, an endoscopic or medical procedure. The preferred gas delivery system includes a heated regulator which automatically controls the temperature of the gas as it leaves a cylinder, and an indicator which indicates the pressure of the gas as it leaves the cylinder. The delivery system may advantageously include a filter for removing foreign material from the gas. The preferred gas delivery system includes a primary heater for heating the gas, a thermostat which allows the user to make fine adjustments to the temperature of the gas, a temperature sensor for monitoring the temperature of the gas as it leaves the primary heater. The preferred gas delivery system further includes a fine pressure regulator which allows the user to adjust the pressure of the gas, and a flow regulator which allows the user to adjust the volumetric flow of gas during the endoscopic procedure. Accurate, responsive indicators connected to the temperature sensor, fine pressure regulator, and flow regulator continuously reflect the temperature, pressure, and volumetric flow rate of the gas.

The preferred gas delivery system is easily connected to standard endoscopic or medical equipment, and is provided with control valves which allow the user to utilize one of several gases during a particular endoscopic or medical procedure.

The preferred gas delivery system can be used in research laboratories to regulate the temperature, volume and pressure of any gas used in tissue culture, bacterial cultures or any time there is a need to accurately control a specific gaseous environment.

Other advantages of the present invention will become apparent to those skilled in the art as the disclosure is made in the following Detailed Description of Preferred Embodiments of the gas delivery system, as illustrated in the accompanying drawing.

DETAILED DESCRIPTION OF THE PREFERRED EMBODIMENTS

In describing a preferred embodiment of the invention illustrated in the drawings, specific terminology will be used for the sake of clarity. However, the invention is not intended to be limited to the specific terms so selected, and it is understood that each specific term includes all technical equivalents which operate in a similar manner to accomplish a similar purpose.

Figure 1:
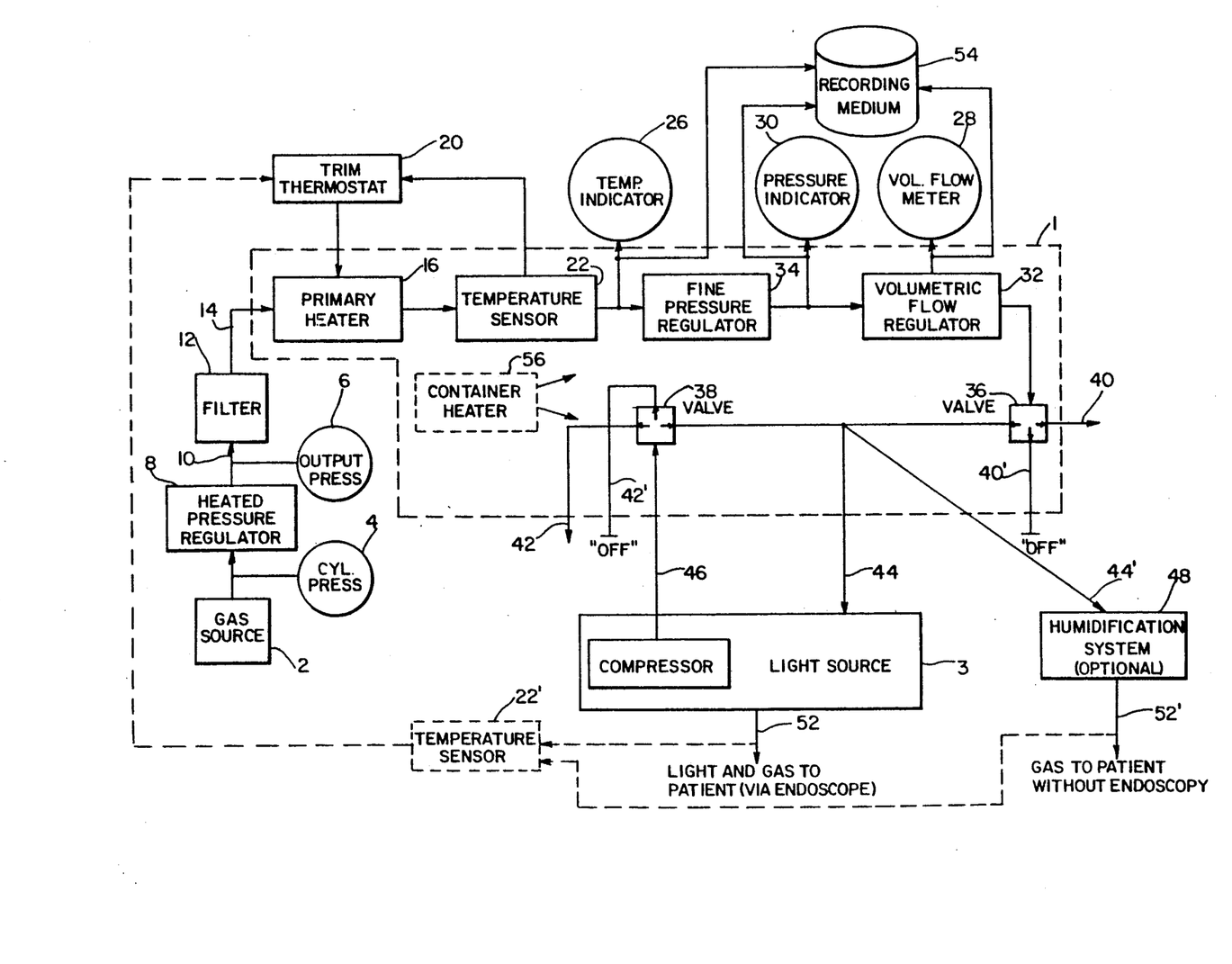
FIG. 1 is a schematic view of the preferred gas delivery system according to the present invention, and illustrates a gas source 2, a light source 3, and an optional humidification system 48 connected to the main body 1 of the gas delivery system.

Referring now to FIG. 1, the main body of the preferred gas delivery system of the present invention is generally designated as element 1. The main body is connected indirectly to a gas source shown as a carbon dioxide ($CO_2$) gas cylinder 2. The main body can also be connected to an optional humidification system 48 if medically indicated, such as a water bath humidifier for oxygen (manufactured by Hudson Oxygen Therapy Sales, Orange Park, Fla.).

The light source is in communication with the patient via a colonoscope or similar device, shown schematically as pathway 52. Briefly, it is a primary function of the preferred embodiment to provide gas from gas source 2 to the patient at the end of path 52, or to another medical instrument at the end of pathway 44', in a manner which is pressure-, volume- and temperature-controlled.

More specifically, the main body 1 of the preferred gas delivery system comprises a block of stainless steel, brass, aluminum, or other medically suitable material. With the possible exception of the gas source 2, cylinder pressure gauge 4, a heated pressure regulator 8, an output pressure gauge 6, a filter 12, and an optional humidification system 48, all elements shown are advantageously integrated into the main block 1 itself. Due to the expendable or replaceable nature of these listed components 2, 4, 6, 8, 12, 26, 28, 30, 48 and 54, it is advisable to retain them as exterior components, rather than integrate them into the main block 1. The integration of the essential components into a single block enables easier control of the temperature of the gas. Also, when integrated into a single block structure, different elements 16, 20, 22, 32, 34, 36, 38 and 56 are advantageously miniaturized, and interconnecting tubing, fittings and leakages are eliminated by use of drilled passages.

In the event that an embodiment is chosen in which the elements are not integrated into a single block, then the elements may be enclosed within a hollow container. Preferably, the container is thermally insulated to minimize loss of heat from gas as it is channelled through the system. Because many of the metallic elements (e.g., valves) of the gas delivery system readily conduct heat to the air surrounding them, it is also advantageous to provide an auxiliary container heating system 56 (auxiliary to the primary gas heater described below) which maintains the particularly effective heat sinks at a temperature closer to desired gas temperature than to ambient temperature. This auxiliary heating is readily implemented using a Smith Gates De-Icer Kit, Smith Gates Corporation, Farmington, Conn. 06032, attached to a heater thermostat by Craftmaster, Model No. 0900718, by Craftmaster Accessories, 18450 South Miles Road, Cleveland, Ohio 44128. Box temperature is controlled using container heater 56 at a setting between 110° F. and 120° F. This temperature is substantially lower than the heating of the gas by primary heater 16. The cord/cable is advantageously wrapped around the heat sink elements in close physical contact, to promote heat conduction from the cord/cable to the valves and fittings.

Referring now to particular elements in FIG. 1, the gas source (element 2) is preferably implemented with a 20 pound $CO_2$ cylinder, manufactured by Kaplan Industries, Route 7 and Morris Avenue, Maple Shade, N.J. 08051. The gas source provides the desired gas, such as $CO_2$, to the gas delivery system for eventual administration to the patient. For the purpose of describing a preferred embodiment, the gas employed is $CO_2$. However, it is to be understood that any medically suitable gas may be used with the present gas delivery system.

Use of a stored gas has the advantages over use of compressed gas from known light sources 3, which employ compressors which deliver gas in a succession of "spurts". Such spurts, either alone or in combination with other factors affecting the pressure of the administered gas, can contribute to patient injury. The use of a gas source 2 with associated control elements as envisioned by the present invention allows gas to be administered in a much more smooth and controlled manner, minimizing possibility of patient injury.

Alternative implementations of the gas source include a local compressed air supply or other medically required compressed gas. Although the invention provides protective mechanisms to ensure proper administration of gas in a safe manner, implementations of the gas source should possess the characteristics that gas be delivered as reliably and smoothly as possible.

The gas source 2 is advantageously provided with a cylinder pressure gauge 4 which indicates the pressure of the gas in the cylinder, from which the amount of available gas can be determined. Such pressure gauges are commonly attached to gas cylinders which are used in medical facilities. An output pressure gauge 6 is also provided to monitor the pressure of the gas as it leaves cylinder 2. The output pressure gauge may be equivalent to a Tomark pressure gauge, manufactured by Tomark, P.O. Box 387, Glendale, S.C. 29436. In general, the gas source output pressure gauge 6 need not be as accurate or responsive as the gas delivery system's main pressure indicator 30 (described below), as gauge 6 does not measure the pressure of the gas which is actually administered to the patient.

The gas source 2 of the preferred gas delivery system is provided with a heated regulator. The heated regulator (element 8 in FIG. 1) is preferably implemented with a heated gas regulator, manufactured by Airco of Virginia Beach, Va., as Part/Model No. 320,8068005. The heated regulator 8 is connected to the output of the gas source 2 to receive the gas, and provides heated gas in a smooth and controlled manner to the filter 12 and the main body 1 of the gas delivery system.

The heated regulator 8 performs the functions of heating the gas and automatically controlling its temperature up to a pre-set limit (such as 100° F.) so that surges in gas flow are minimized in quantity and magnitude. In a preferred embodiment, the heated regulator maintains the $CO_2$ gas at an elevated temperature to prevent "freeze up." Freeze-up is a phenomenon of cooling of equipment which is observed as a result of the refrigerant action of evaporating liquified gas, particularly $CO_2$. Absent the safeguards in the present scenario, "freeze up" would be accompanied by sputtering, or fluctuation in the pressure of the gas, due to a surge of liquified gas suddenly changing to a gaseous state. The heated regulator advantageously prevents any liquid $CO_2$ from passing out of the cylinder toward the main body of the gas delivery system. Such liquified gas might otherwise cause a dangerous fluctuation in the temperature and/or pressure of the gas ultimately administered to the patient.

In the preferred embodiment, the heated regulator 8 contains an internal filter, designed to ensure that only gas passes through it. Imperfections in the internal filtering mechanism, and the potentially disastrous consequences of a filter failure, make it advisable to supplement the internal filter of the heated regulator 8 with a separate filter 12, to be described in greater detailer below. The heated regulator system is thus "fail-safe," possessing an over-pressure safety relief valve, and is pre-set at 100° F., protecting the gas delivery system and the patient from malfunctions in the gas source and associated regulator. Implementations of the heated regulator 8 should possess the characteristics that are fail-safe, durable and easy to operate.

Tubing connects the heated regulator 8 on gas source 2 to provide gas to filter 12. The tubing 10 may be implemented with a 0.25-inch outside diameter polyethylene tubing, manufactured by Tubing Corporation, a division of Beacon Hose Manufacturing Company, Charlotte, N.C. 28208.

The tubing 10 (and tubing used generally throughout the device, unless otherwise noted) performs the function of carrying gas from a source to a destination. Alternative implementations of certain lengths of the tubing include passageways integrally cut or bored into the material (e.g., stainless steel) which comprises the body of the gas delivery system. For connections outside the main body of the gas delivery system, alternative implementations of tubing include insulated copper, brass or stainless steel tubing or polyvinyl chloride tubing, depending on the medical requirements of the gas being used. Implementations of the tubing 10 should also possess the characteristics that they minimize heat loss to the environment.

Minimization of heat loss to the environment facilitates predictive temperature control of the gas, which is primarily heated within the gas delivery system body 1 before traversing progressively thin channels before reaching the patient. Tubing which is external to the main block 1 (and tubing within a container, if the body is not of unitary construction) is preferably thermally insulated, using, for example, 0.25" outside diameter polypropylene tubing, Model No. PP430500, by Parker Hose Division, 30240 Lakeland Drive, Wickliffe, Ohio 44092. Other desirable tubing characteristics include being inert to the gas being used, durability and approval for medical use.

A filter 12 removes foreign matter from the gas prior to the gas entering the body of the delivery system 1. The filter 12 is preferably implemented with a gas filter manufactured by Wilkerson Corporation, of P.O. Box 127, Englewood, Colo. 80150, as Part/Model No. F00-02-000. The filter 12 is connected to the heated regulator 8 to receive heated gas, and provides pure, filtered gas to a primary heater 16.

The filter 12 supplements any filter in the heated regulator 8 in removing undesired substances which may have entered the gas. (Such substances may include water droplets, or metal fragments inadvertently expelled from the gas source 2 into the gas.) Implementations of the filter 12 should allow removal of moisture and metallic filings, be easily replaceable, and be compatible with the gas being used.

Gas passes through tubing 14 from filter 12 to the primary heater 16. The primary heater 16 may be implemented with a heater having the characteristics of a heater manufactured by CalCo Controls, Inc., 316 Cary Point Drive, Cary, Ill., 60013 as Model No. 300F, Part No. RME-3-1 ($CO_2$, CGA 320; 300 cu ft/hr). The primary heater 16 heats the smoothly flowing, filtered gas to a desired temperature.

For reasons described elsewhere in this specification, it is preferable in many scenarios that the temperature as it enters the patient be the body temperature of the patient, so that the endoscopic or medical procedure is carried out under physiologic, or near-physiologic, conditions. However, it is understood that the present invention may be practiced using any desired gas temperature, including temperatures which may be different from the patient's body temperature.

Generally, the temperature of the gas at the primary heater 16 will be different than the gas at the point of administration to the patient, at the end of path 52. The heat loss between primary heater 16 and the point of administration may be approximately 32° F,, as in the case of colonoscopy. Heat loss for other medical procedures may be less depending on the amount of heat sink from the instrument attached to the output of main block 1. Concerning colonoscopy, due to these heat losses to atmosphere, to the light source and to the endoscopic components which are lower than body temperature, the temperature of the gas at the primary heater 16 will generally have to be set higher than body temperature. The degree of heat loss may be measured empirically for each given set of equipment.

Unpredictability or variation of heat loss are minimized by insulating any tubes which are external to the equipment, and by controlling the temperature of the equipment through which the gas must pass before being administered to the patient. In embodiments in which the main body 1 of the gas delivery system is a block of, e.g., of insulated stainless steel, the task of minimizing (or at least predictably controlling) heat loss is facilitated by controlled heating of the unchanging physical configuration of the device.

Enhancement of control of the temperature of the primary heater gas is achieved by feedback of actual gas temperature measurements made at or near the point of administration, along path 52. In such an embodiment, the temperature sensor 22 is replaced by a temperature sensor 22' along path 52, and feeds trim thermostat 20. The temperature sensor 22' may be, for example, on adapted 240" Ranco 060-100 capillary and bulb sensor thermostat, manufactured by Ranco Control, 8115 U.S. Route 42N, Plain City, Ohio 43064.

Trim thermostat 20, when used in conjunction with temperature sensor 22', is calibrated to reflect a greater difference in temperature between measured temperature (at 52) and heater temperature (at 16) than if temperature sensor 22 is employed, as will readily be appreciated by those skilled in the art. In any of these temperature feedback control methods, the gas finally administered to the patient may be controlled to a medically optimum temperature.

Other heaters associated with the gas delivery system, such as the heater in heated regulator 8 and the heating elements used in conjunction with the container heater 56 (described above), are considered auxiliary in function to primary heater 16. It is the primary responsibility of primary heater 16 to heat the gas to the temperature which will ultimately cause the administered gas to be of the desired temperature as required by the physician.

Implementations of the primary heater 16 should also possess the characteristic that it reliably heat the gas in a controlled and accurate manner. In a preferred embodiment, primary heater 16 is provided with an internal safety mechanism which has been pre-set at a maximum safe temperature of, for example, 170° F.

The heating element of the heater 16 is controlled by a trim thermostat 20. Trim thermostat 20 allows the user to make fine adjustments in the temperature of the gas prior to delivering the gas to a patient. Small adjustments which can be made by means of trim thermostat 20 will have no appreciable effect on the pressure or volume of the gas delivered to the patient. In order to accommodate a wide range of uses, the trim thermostat preferably has a temperature range of at least between 80° F. and 160° F.

A temperature sensing unit 22 is attached to the output of primary heater 16. The temperature sensing unit 22 is the capillary tube and bulb sensing portion of the trim thermostat 20, preferably implemented with a Series A19, manufactured by Johnson Controls Inc., Control Products Division, 1302 East Monroe Street, Goshen, Ind. 46526. In one embodiment, a capillary and sensor bulb are attached to the trim thermostat is disposed within a tube, which is itself disposed within a larger tube through which the heated gas exits the primary heater 16. The effect of the heated gas on the capillary tube and sensor bulb indicates to the trim thermostat the temperature of the gas.

Alternative implementations of the temperature sensing unit 22 include electronic sensors such as those manufactured by Ranco Corporation. Implementations of the temperature sensing unit 22 should possess the characteristics that they be accurate and reliable over at least the entire temperature range which is envisioned in the gas delivery application (e.g., from 80° F. to 170° F.).

The temperature indicator 26 provides a visual reading of the gas temperature to the physician or other user. The temperature indicator 26 is mounted at the outlet 24 of the temperature sensing unit 22. The indicator continuously indicates the current temperature of the gas output from the primary heater 16, and, by implication, an offset indication of the temperature of the gas being administered to a patient. Preferably, the temperature is displayed by means of a light emitting diode (LED) displays, although use of analog, mechanical gauges lies within the contemplation of the present invention. One example of such a gauge is a thermometer, manufactured by Dresser Industries Instrument Division, Dresser Ind. Inc., Stratford, Conn. 06497, as Type 91. Alternative implementations of the temperature indicator 26 include the use of electronic sensors with LED read-out.

Implementations of the temperature indicator 26 should, of course, be reliable and accurate over the entire temperature range to be encountered by the gas delivery system. Like any indicator in the gas delivery system, they should also be responsive to changes in temperature (or other parameter under measurement), so that the physician is immediately alerted to malfunctions in the equipment. Immediate warning to the physician will allow him or her to take corrective action to prevent injury to the patient or damage to the gas delivery system.

After the heated gas leaves the primary heater 16 through the temperature sensing unit 22, it passes via a passageway cut into the body 1, or via tubing (e.g., plastic tubing) to a fine pressure regulator 34.

The fine pressure regulator 34 is preferably implemented with a fine pressure regulator, manufactured by Asco of P.O. Box 417, Woodbridge, N.J. 07095, as Part/Model No. 4406-B. The fine pressure regulator 34 provides pressure-regulated gas to a flow regulator 32. The fine pressure regulator 34 accurately regulates the pressure of the gas before it is finally administered to the patient.

Alternative implementations of the fine pressure regulator 34 include other standard gas control pressure regulators which are used in the medical field most often for oxygen gas, but applicable to $CO_2$ gas as well. Implementations of the fine pressure regulator 34 should possess the characteristic that they be extremely reliable in operation, as uncontrolled surges in pressure may cause injury to the patient as serious as perforation of the bowel. The use of double regulators and temperature controls prevents this.

In a manner conceptually similar to heated pressure regulator 8, the fine pressure regulator 34 also contains a relief valve as a safety feature. The relief valve offers an alternative path for escape of gas during an over-pressure condition, thereby reducing injury to the patient and damage to the apparatus.

An accurate pressure indicator 30 is provided to indicate the pressure being delivery to a patient after the gas has heated to the adjusted temperature by primary heater 16 and has been adjusted in pressure by fine pressure regulator 34. The pressure indicator 30 is preferably implemented with an indicator equivalent to an Ashcroft Type 1190, manufactured by Dresser Ind. Inc., Stratford, Conn. 06497. The pressure indicator 30 is connected to the fine pressure regulator 34 output to receive the heated and pressure-regulated gas, and provides an indication of the gas pressure to the physician.

The pressure on this indicator is either substantially identical to the pressure of the gas which is actually delivered to the patient, or a translated pressure depending on the medical equipment or medical procedure being performed on a patient.

Preferred implementations of the pressure indicator 30 include LED indicators, although use of mechanical, analog pressure gauges such as the unit cited above lie within the contemplation of the invention. Implementations of the pressure indicator 30 should reliably, accurately, and responsively indicate the pressure of the gas throughout the pressure range expected in a gas delivery system scenario.

The gas flows from the fine pressure regulator 34 through a volume control flow regulator 32. An attached flow meter 28 measures the volumetric rate of the flow of the gas being delivered to the patient (e.g., in liters per minute).

The flow regulator 32 with meter 28 are preferably implemented with an Airco regulator, manufactured by Airco, 1501 Harpers Road, Virginia Beach, Va. 23454, as Part/Model No. ADI 2211. The flow regulator 32 with meter 28 provides a controlled volume of gas per unit time to the patient, while indicating the volumetric rate of flow to the physician.

The flow meter 28 performs the function of continuously indicating to the physician the volumetric rate of flow, so that he or she can take corrective action to prevent patient injury or equipment damage in the event of equipment malfunction, or to change volume flow depending on the individual patient.

Alternative implementations of the flow regulator 32 with meter 28 include electronic LED systems. Implementations of the flow regulator 32 with meter 28 should reliably, accurately, and responsively indicate the volumetric flow rate of the gas throughout the volume range expected in a gas delivery system scenario.

Those skilled in the art will appreciate how the primary heater 16, the fine pressure regulator 34, and the volumetric flow regulator 32 control the temperature, pressure, and volumetric flow rate, respectively, of the gas which is administered to the patient. As will also be appreciated by those skilled in the art, the particular ordering of these three named elements need not be as particularly presented above, but may be re-arranged to meet medical, manufacturing, physical, or other constraints.

The active, regulating components of the preferred gas delivery system have safety mechanisms. These safety mechanisms serve to prevent injury to the patient and damage to the device, in the event the component experiences a failure (such as an overheating or over-pressure condition). The following values of pressure, volumetric flow rate, or temperature relief thresholds are believed desirable in gas delivery systems for use in endoscopic or medical procedures:

| | |
|---|---|
| Heated pressure regulator 8 (normal range: 0–30 psi) | 10 psi; 100° F. |
| Primary heater 16 (normal range: 80–170° F.) | 170° F. |
| Fine pressure regulator 34 (normal range: 0–15 psi) | up to 6 psi |
| Flow regulator 32 (normal range: 0–15 l/m) | up to 11 l/m |

In the event that electronic sensors are used, a voltage regulator (not shown) for the entire system is desirable, inasmuch as voltage spikes could cause any of the electronic regulatory elements to malfunction.

The indication or control devices of the preferred gas delivery system have display ranges which encompass the range of parameter values (pressure, temperature, volumetric flow rate) expected in a particular operational scenario. The following ranges are believed desirable in gas delivery systems for use in endoscopic or medical procedures:

| | |
|---|---|
| Pressure gauge 6 | 0–60 psi |
| Trim thermostat 20 | 80–160° F. |
| Temperature indicator 26 | 0–250° F. |
| Pressure indicator 30 | 0–15 psi |
| Volumetric flow meter 28 | 0–15 l/m |

The main body 1 of the preferred gas delivery system is provided with first and second control valves 36 and 38, and corresponding first and second vents 40 and 42.

The first valve 36 is preferably implemented with a three-way brass valve, manufactured by Everco Valves, Everco Industries, Inc., Lincolnwood, Ill. 60646. The first valve 36 is connected to the flow regulator 32 to receive the temperature-, pressure- and volume-regulated gas, and channels it along one of two pathways or an OFF position 42', depending on the user-chosen setting of the valve 36. A first path leads, ultimately, to the patient, first by way of tube 44 which carries the gas out of delivery system main body 1. A second path for the regulated gas is to be vented to the atmosphere by way of first vent 40. Vent 40 allows the first valve 36 to vent the controlled gas to atmosphere at those instants where it is not to be directed for administration to the patient. Pathway 40' is the OFF position.

The second valve 38 may be implemented with a valve of the same type as first valve 36. The second valve 38 is connected along tubing path 46 to the output of the compressor of the external endoscopic light source 3 to receive gas which is volume- and pressure-regulated only by the pre-set limits of the air compressor in the light source. Thus, the gas entering the first valve 36 from the flow regulator 32 will be a much better controlled entity than the gas entering the second valve 38 from known light source equipment 3.

The second valve 38 channels the gas from path 46 along one of two pathways, plus an OFF position, depending on the user-chosen setting of the valve 38. A first path leads ultimately to the patient, first by way of tube 44 which carries the gas back to the light source. A second path is to be vented to the atmosphere by way of second vent 42, which connected to the second valve 38. 42' is the OFF position.

Together, the first valve 36 and the second valve 38 perform the function of directing a desired gas for administration to the patient. Advantageously, the illustrated exemplary arrangement of valves allows the user various options in administering gas to a patient during an endoscopic or medical procedure. For example, vent 40 is provided to allow the user to warm up a gas to a pre-set temperature, pressure and volume prior to an endoscopic or medical procedure. The gas which has not yet reached the proper temperature, pressure and flow rate is harmlessly vented to atmosphere. Specifically, the second valve enables the physician to employ gas provided by the compressor unit in the light source 3 unchanged. Pathway 44' to an optional humidification system 48, routed via 52' to a patient with the use of medical instruments other than endoscopes, is depicted in FIG. 1. This pathway can also be fed back with temperature sensor 22' for control of temperature of a medically administered gas.

In a preferred embodiment, the physician is thus allowed independent control of the first and second valves 36 and 38. Valve 36 controls cylinder gas according to accurate volume, temperature and pressure. Valve 38 controls air from the light source but only to the limits pre-set by the light source air compressor. Either of the valves can be used and any medically necessary gas can be used as the gas source. It is possible, therefore, that both valves could allow forced gas to enter their common output path 44. The pressures are prevented from becoming additive (a potentially dangerous circumstance, for the patient), however, by the fine pressure regulator 34 according to the present invention. (It is possible that the external source, such as light source 3, may also have a pressure regulation mechanism added, thus preventing over-pressure conditions from arising in paths leading directly to the patient.)

Of course, alternative components and arrangements of valves allowing chosen "make-before-break" or "break-before-make" functions, as found desirable under the circumstances. Such alternative embodiments include a single valve, external to the main body 1, which switches between the output of flow regulator 32 and the output of the light source compressor on path 46. This embodiment may also include a third setting, an "off" setting to restrain any gas at all from being administered to the patient.

The gas delivery system may include an optionally heated humidification system, such as a closed, insulated and heated water bath through which the gas passes prior to entering the patient. The humidification system 48 is preferably implemented with a water bath humidifier, by Hudson Oxygen Therapy Sales, Orange Park, Fla. The optional humidification system 48 is connected to the pathway 44' leading from valves 36 and 38 to receive the gas intended for administration for the patient via 52'.

The humidification system 48 elevates the humidity of the administered gas, so that it is possible to carry out procedures on organs such as the lungs, where introduction of dry gas might be physiologically harmful. Implementations of the humidification system 48 should possess the characteristics that the pressure, temperature, and volume of the gas reaching the patient is not substantially altered. To this end, the gas flowing into the humidification system may be percolated through a water bath which is heated to a temperature which will not cause defeat of the temperature control measures of the gas delivery system according to the present invention.

In the illustrated embodiment, the humidification system 48 is connected in-line between the main body 1 of the gas delivery system and the patient. Humidification of the gas is not needed for endoscopic purposes. The humidification system is external to the main block 1 for purposes of easy cleaning and respectability.

According to the present invention, then, the physician or other user can observe the actual temperature, pressure and volumetric flow rate of the gas that is being used on indicators (or gauges) 26, 28, and 30. However, for documentation purposes, the three sets of measurements which are produced during the procedure by the indicators 26, 28, and 30 are connected to a recording medium 54. The recording medium 54 may be any system such as a visual display with attached video cassette recorder, any magnetic or optical media such as magnetic or optical disk drives, or a hard-copy print-out recording system such as those used in electrocardiograms.

The recording of the outputs of this comprehensive electronic sensing system built into the gas delivery system both provides a real time display and allows permanent recordation of the continuously read-out data regarding temperature, pressure, and volumetric flow rate. This comprehensive observation and documentation capability provides the physician with a complete record of the entire procedure. The record can be placed with the patient's chart for future evaluation, diagnosis and treatment.

This record also becomes invaluable in the event that a complication develops with the patient during the procedure. The association of an event with the temperature, pressure, and volumetric flow rate data might help to isolate the cause of the deleterious event. This is a significant improvement over the present state of the art delivery systems since, prior to the present system, it was not possible to quantitatively determine o record critical data such as the exact temperature, pressure and volumetric flow rate of the gas delivered to the patient.

Finally, the total quantity of gas used or the amount remaining can be calculated using the difference between the cylinder pressure read-out of the compressed gas source from the beginning of the procedure until the end of the procedure.

The present invention provides medical procedures which may be practiced, using gas delivery systems as described above. Thus, for example, the invention encompasses a method of safely delivering a gas to a patient during a medical procedure, the method comprising the steps of activating a gas delivery system comprising a primary heater, a fine pressure regulator, and a volumetric flow regulator with corresponding temperature indicator, pressure indicator, and volumetric flow rate indicator; observing one or more of the temperature indicator, pressure indicator, and volumetric flow rate indicator; conducting the medical procedure while periodically monitoring one or more of the temperature indicator, pressure indicator, and volumetric flow rate indicator; and adjusting one or more of the primary heater, fine pressure regulator, and volumetric flow regulator as needed during the medical procedure. A humidification system is optional.

From the above, it is apparent that many modifications and variations of the present invention are possible in light of the above teachings. It is, therefore, to be understood that, within the scope of the appended claims, the invention may be practiced otherwise than as specifically described.

What is claimed is:

1. A gas delivery system for use in an endoscopic or medical procedure involving a patient, comprising:

a gas source supplying gas for use in the endoscopic or medical procedure;

a heated pressure regulator, connected to and receiving gas from the gas source, for pre-heating the gas to ensure that it is in its gaseous state and for initially regulating the pressure of the gas;

a gas source output pressure gauge, connected to the heated pressure regulator, for measuring the pressure of the gas output through the heated pressure regulator;

a filter, connected to the heated pressure regulator, for receiving the heated gas from the heated pressure regulator and filtering out foreign matter from the gas;

a gas delivery system main body, connected to an output of the filter for receiving filtered gas, comprising:

(a) a primary heater for heating the gas from the filter to a temperature having a relationship to a physiologically desired temperature for administration to the patient;

(b) a temperature sensor, connected to an output of the primary heater, for measuring the temperature of the gas exiting the primary heater;

(c) a thermostat, connected to an output of the temperature sensor and to an input of the primary heater, for receiving temperature measurements from the temperature sensor, for governing the primary heater in regulating the temperature of the gas;

(d) a fine pressure regulator, for controlling the pressure of the gas administered to the patient in the endoscopic or medical procedure; and (e) a volumetric flow regulator, for controlling the volumetric flow rate of the gas administered to the patient in the endoscopic or medical procedure;

wherein the primary heater, fine pressure regulator, and volumetric flow regulator are connected substantially in series, not necessarily in the recited order;

a temperature indicator, a pressure indicator, and a flow meter, connected, respectively, to the temperature sensor, the fine pressure regulator, and the volumetric flow regulator, for respectively indicating the temperature, pressure and volumetric flow rate of the gas;

a recording medium, connected to the temperature sensor, fine pressure regulator and volumetric flow regulator, for recording the temperature, pressure, and volumetric flow rate of the gas as a function of time during the endoscopic or medical procedure;
an endoscopic light source comprising a compressed air source for producing compressed air as an alternative gas; and
a valve assembly, connected to the main body and to the endoscopic light source, for controllably directing either (1) the gas from the main body, or (2) the compressed air from the endoscopic light source compressed air source, into an endoscope for administration to the patient.

2. A gas delivery system, comprising, in combination:
a gas source;
a heater for heating gas from the gas source to a desired temperature;
a pressure regulator for controlling the pressure of the gas;
a volumetric flow regulator for controlling the volumetric flow rate of the gas; and
a temperature indicator, a pressure indicator, and a flow meter, connected, respectively, to the heater, the pressure regulator, and the volumetric flow regulator, for indicating the temperature, pressure and volumetric flow rate of the gas;
wherein the heater, pressure regulator, and volumetric flow regulator are connected substantially in series after the gas source, not necessarily in the recited order, so as to provide a delivered gas.

3. The gas delivery system of claim 2, wherein the gas source comprises a cylinder containing any medically suitable gas such as carbon dioxide, for controlled administration to a patient during an endoscopic or medical procedure.

4. The gas delivery system of claim 3, further comprising a heated regulator connected to an output of the gas source for ensuring that gas exiting the gas source through the output does not undergo substantial variations in pressure as a result of changing from liquid state to gaseous state.

5. The gas delivery system of claim 3, further comprising a filter, connected between (1) the gas source, and (2) the heater, pressure regulator and volumetric flow regulator, for filtering out particles or other unwanted matter from the gas.

6. The gas delivery system of claim 2, further comprising:
a temperature sensor, connected to an output of the heater, for measuring the temperature of the gas exiting the heater; and
a thermostat, connected to an output of the temperature sensor to receive temperature measurements from the temperature sensor, and connected to an input of the heater for governing the heater in regulating the temperature of the gas.

7. The gas delivery system of claim 2, further comprising a recording medium, connected to the temperature sensor, pressure regulator, and volumetric flow regulator, for receiving temperature, pressure, and volumetric flow rate information, respectively, for documenting an endoscopic or medical procedure in which the gas delivery system is involved.

8. The gas delivery system of claim 2, further comprising an endoscopic light source compressor for producing compressed air as delivered by the source for an endoscopic or medical procedure as a source of delivered gas which is a possible alternative to the gas delivered by the combination of the heater, pressure regulator, and volumetric flow regulator.

9. The gas delivery system of claim 8, further comprising a valve assembly, the valve assembly connected to an output of the combination of the heater, pressure regulator, and volumetric flow regulator, the valve assembly also connected to an output of the endoscopic light source compressor, for selectively routing either (1) gas from the gas source after passing through the heater, pressure regulator and volumetric flow regulator, or (2) the compressed air from the endoscopic light source compressor, to a patient during the endoscopic or medical procedure.

10. The gas delivery system of claim 2, further comprising a humidification system, connected to an output of the combination of the heater, pressure regulator, and volumetric flow regulator, for increasing the humidity of a gas selected for administration to a patient.

11. A gas delivery system, comprising, in combination:
a gas source;
a heater for affirmatively controlling the temperature of the gas from the gas source;
a pressure regulator, for affirmatively controlling the pressure of the gas; and
a volumetric flow regulator, for affirmatively controlling the volumetric flow rate of the gas;
wherein the heater, pressure regulator, and volumetric flow regulator are connected substantially in series after the gas source, not necessarily in the recited order, to provide a delivered gas from the system; and
wherein the temperature, pressure, and volumetric flow rate of the delivered gas are simultaneously quantitatively controlled.

12. The gas delivery system of claim 11, wherein the gas source comprises a cylinder containing any medically suitable gas such as carbon dioxide, for controlled administration to a patient during an endoscopic or medical procedure.

13. The gas delivery system of claim 12, further comprising a heated regulator connected to an output of the gas source for ensuring that gas exiting the gas source through the output does not undergo substantial variations in pressure as a result of changing from liquid state to gaseous state.

14. The gas delivery system of claim 12, further comprising a filter, connected between (1) the gas source, and (2) the heater, pressure regulator and volumetric flow regulator, for filtering out particles or other unwanted matter from the gas.

15. The gas delivery system of claim 11, further comprising:
a temperature sensor, connected to an output of the heater, for measuring the temperature of the gas exiting the heater; and
a thermostat, connected to an output of the temperature sensor to receive temperature measurements from the temperature sensor, and connected to an input of the heater for governing the heater in regulating the temperature of the gas.

16. The gas delivery system of claim 11, further comprising a recording medium, connected to the temperature sensor, pressure regulator, and volumetric flow regulator, for receiving temperature, pressure, and volumetric flow rate information, respectively, for documenting an endoscopic or medical procedure in which the gas delivery system is involved.

17. The gas delivery system of claim 11, further comprising an endoscopic light source compressor for producing compressed air as delivered by the source for an endoscopic or medical procedure as a source of delivered gas which is a possible alternative to the gas delivered by the combination of the heater, pressure regulator, and volumetric flow regulator.

18. The gas delivery system of claim 17, further comprising a valve assembly, the valve assembly connected to an output of the combination of the heater, pressure regulator, and volumetric flow regulator, the valve assembly also connected to an output of the endoscopic light source compressor, for selectively routing either (1) gas from the gas source after passing through the heater, pressure regulator and volumetric flow regulator, or (2) the compressed air from the endoscopic light source compressor, to a patient during the endoscopic or medical procedure.

19. The gas delivery system of claim 11, further comprising a humidification system, connected to an output of the combination of the heater, pressure regulator, and volumetric flow regulator, for increasing the humidity of a gas selected for administration to a patient.

20. A gas delivery system for use in an endoscopic procedure, the system comprising, in combination:
- a gas source for containing gas suitable for introduction into a patient's body for the endoscopic procedure;
- a heater for affirmatively controlling the temperature of the gas from the gas source;
- a pressure regulator, for affirmatively controlling the pressure of the gas;
- a volumetric flow regulator, for affirmatively controlling the volumetric flow rate of the gas; and
- a connecting pathway for providing delivered gas from the system to endoscopic equipment used in the endoscopic procedure;
- wherein the heater, pressure regulator, and volumetric flow regulator are connected substantially in series after the gas source, not necessarily in the recited order, to provide the delivered gas from the system; and
- wherein the temperature, pressure, and volumetric flow rate of the delivered gas are simultaneously quantitatively controlled.

21. The gas delivery system of claim 20, wherein the gas source comprises a cylinder containing any medically suitable gas such as carbon dioxide, for controlled administration to a patient during the endoscopic procedure.

22. The gas delivery system of claim 21, further comprising a heated regulator connected to an output of the gas source for ensuring that gas exiting the gas source through the output does not undergo substantial variations in pressure as a result of changing from liquid state to gaseous state.

23. The gas delivery system of claim 21, further comprising a filter, connected between (1) the gas source, and (2) the heater, pressure regulator and volumetric flow regulator, for filtering out particles or other unwanted matter from the gas.

24. The gas delivery system of claim 20, further comprising:
- a temperature sensor, connected to an output of the heater, for measuring the temperature of the gas exiting the heater; and
- a thermostat, connected to an output of the temperature sensor to receive temperature measurements from the temperature sensor, and connected to an input of the heater for governing the heater in regulating the temperature of the gas.

25. The gas delivery system of claim 20, further comprising a recording medium, connected to the temperature sensor, pressure regulator, and volumetric flow regulator, for receiving temperature, pressure, and volumetric flow rate information, respectively, for documenting the endoscopic procedure in which the gas delivery system is involved.

26. The gas delivery system of claim 20, further comprising an endoscopic light source compressor for producing compressed air as delivered by the source for the endoscopic procedure as a source of delivered gas which is a possible alternative to the gas delivered by the combination of the heater, pressure regulator, and volumetric flow regulator.

27. The gas delivery system of claim 26, further comprising a valve assembly, the valve assembly connected to an output of the combination of the heater, pressure regulator, and volumetric flow regulator, the valve assembly also connected to an output of the endoscopic light source compressor, for selectively routing either (1) gas from the gas source after passing through the heater, pressure regulator and volumetric flow regulator, or (2) the compressed air from the endoscopic light source compressor, to a patient during the endoscopic procedure.

28. The gas delivery system of claim 20, further comprising a humidification system, connected to an output of the combination of the heater, pressure regulator, and volumetric flow regulator, for increasing the humidity of a gas selected for administration to a patient.

29. A carbon dioxide delivery system for use in an endoscopic procedure, the system comprising, in combination:
- a carbon dioxide source for containing carbon dioxide for introduction into a patient's body for the endoscopic procedure;
- a heater for affirmatively controlling the temperature of the carbon dioxide from the carbon dioxide source;
- a pressure regulator, for affirmatively controlling the pressure of the carbon dioxide;
- a volumetric flow regulator, for affirmatively controlling the volumetric flow rate of the carbon dioxide; and
- a connecting pathway for providing delivered carbon dioxide from the system to endoscopic equipment used in the endoscopic procedure;
- wherein the heater, pressure regulator, and volumetric flow regulator are connected substantially in series after the carbon dioxide source, not necessarily in the recited order, to provide the delivered carbon dioxide from the system; and
- wherein the temperature, pressure, and volumetric flow rate of the delivered carbon dioxide are simultaneously quantitatively controlled.

30. The carbon dioxide delivery system of claim 29, wherein the carbon dioxide source comprises a cylinder containing the carbon dioxide for controlled administration to a patient during the endoscopic procedure.

31. The carbon dioxide delivery system of claim 30, further comprising a heated regulator connected to an output of the carbon dioxide source for ensuring that carbon dioxide exiting the carbon dioxide source through the output does not undergo substantial variations in pressure as a result of changing from liquid state to gaseous state.

32. The carbon dioxide delivery system of claim 30, further comprising a filter, connected between (1) the carbon dioxide source, and (2) the heater, pressure regulator and volumetric flow regulator, for filtering out particles or other unwanted matter from the carbon dioxide.

33. The carbon dioxide delivery system of claim 29, further comprising:
   a temperature sensor, connected to an output of the heater, for measuring the temperature of the carbon dioxide exiting the heater; and
   a thermostat, connected to an output of the temperature sensor to receive temperature measurements from the temperature sensor, and connected to an input of the heater for governing the heater in regulating the temperature of the carbon dioxide.

34. The carbon dioxide delivery system of claim 29, further comprising a recording medium, connected to the temperature sensor, pressure regulator, and volumetric flow regulator, for receiving temperature, pressure, and volumetric flow rate information, respectively, for documenting the endoscopic procedure in which the carbon dioxide delivery system is involved.

35. The carbon dioxide delivery system of claim 29, further comprising an endoscopic light source compressor for producing compressed air as delivered by the source for the endoscopic procedure as a source of delivered carbon dioxide which is a possible alternative to the carbon dioxide delivered by the combination of the heater, pressure regulator, and volumetric flow regulator.

36. The carbon dioxide delivery system of claim 35, further comprising a valve assembly, the valve assembly connected to an output of the combination of the heater, pressure regulator, and volumetric flow regulator, the valve assembly also connected to an output of the endoscopic light source compressor, for selectively routing either (1) carbon dioxide from the carbon dioxide source after passing through the heater, pressure regulator and volumetric flow regulator, or (2) the compressed air from the endoscopic light source compressor, to a patient during the endoscopic procedure.

37. The carbon dioxide delivery system of claim 29, further comprising a humidification system, connected to an output of the combination of the heater, pressure regulator, and volumetric flow regulator, for increasing the humidity of a gas selected for administration to a patient.

38. A gas delivery system, comprising, in combination:
   a gas source;
   a heater for affirmatively controlling the temperature of the gas from the gas source;
   a pressure regulator, for affirmatively controlling the pressure of the gas; and
   a volumetric flow regulator, for affirmatively controlling the volumetric flow rate of the gas;
   wherein the heater, pressure regulator, and volumetric flow regulator are connected substantially in series after the gas source, not necessarily in the recited order, to provide a delivered gas from the system;
   wherein the heater, pressure regulator, and volumetric flow regulator are contained within a single cabinet, providing the only substantial affirmative control of the temperature, pressure, and volumetric flow rate of the delivered gas; and
   wherein the temperature, pressure, volumetric flow rate of the delivered gas are simultaneously quantitatively controlled.

39. A method of safely delivering a gas to a patient, comprising the steps of:
   activating a gas delivery system comprising a heater, a pressure regulator and a volumetric flow regulator with corresponding and respectively connected temperature indicator, pressure indicator, and volumetric flow rate indicator, wherein the heater, pressure regulator and volumetric flow regulator are connected substantially in series, not necessarily in the recited order;
   observing one or more of the temperature indicator, pressure indicator and volumetric flow rate indicator;
   conducting a medical procedure while periodically monitoring one or more of the temperature indicator, pressure indicator and volumetric flow rate indicator; and
   adjusting one or more of the heater, pressure regulator and volumetric flow regulator as needed, to thereby simultaneously and affirmatively control the temperature, pressure, and volumetric flow rate of the gas delivered to the patient.

40. A method of safely delivering a gas to a patient, comprising the steps of:
   activating a gas delivery system comprising a heater, a pressure regulator and a volumetric flow regulator with corresponding and respectively connected temperature indicator, pressure indicator, and volumetric flow rate indicator, and a humidification system, wherein the heater, pressure regulator and volumetric flow regulator are connected substantially in series, not necessarily in the recited order, and the humidification system is connected to an output of the combination of the substantially series-connected heater, pressure regulator and volumetric flow regulator;
   observing one or more of the temperature indicator, pressure indicator and volumetric flow rate indicator;
   conducting a medical procedure while periodically monitoring one or more of the temperature indicator, pressure indicator and volumetric flow rate indicator; and
   adjusting one or more of the heater, pressure regulator and volumetric flow regulator as needed, to thereby simultaneously and affirmatively control the temperature, pressure, and volumetric flow rate of the gas delivered to the patient.

41. A method of safely delivering a gas to a patient, comprising the steps of:
   activating a gas delivery system comprising a heater, a pressure regulator and a volumetric flow regulator with corresponding and respectively connected temperature indicator, pressure indicator, and volumetric flow rate indicator, wherein the heater, pressure regulator and volumetric flow regulator are connected substantially in series, not necessarily in the recited order;
   observing one or more of the temperature indicator, pressure indicator and volumetric flow rate indicator;
   conducting an endoscopic procedure while periodically monitoring one or more of the temperature indicator, pressure indicator and volumetric flow rate indicator; and
   adjusting one or more of the heater, pressure regulator and volumetric flow regulator as needed, to thereby simultaneously and affirmatively control the temperature, pressure, and volumetric flow rate of the gas delivered to the patient.

* * * * *

UNITED STATES PATENT AND TRADEMARK OFFICE
CERTIFICATE OF CORRECTION

PATENT NO. : 5,006,109

DATED : April 9, 1991

INVENTOR(S) : Donald D. Douglas et al.

It is certified that error appears in the above-identified patent and that said Letters Patent is hereby corrected as shown below:

On the title page and in column 1, line 4, in the title, delete the word "INSUFFICATION" and insert therefor --INSUFFLATION--.

Signed and Sealed this

Twentieth Day of October, 1992

Attest:

DOUGLAS B. COMER

Attesting Officer     Acting Commissioner of Patents and Trademarks